(12) United States Patent
Honaryar

(10) Patent No.: US 9,089,395 B2
(45) Date of Patent: Jul. 28, 2015

(54) PRE-LOADED SEPTUM FOR USE WITH AN ACCESS PORT

(75) Inventor: Babak Honaryar, Orinda, CA (US)

(73) Assignee: APPOLO ENDOSURGERY, INC., Austin, TX (US)

( * ) Notice: Subject to any disclaimer, the term of this patent is extended or adjusted under 35 U.S.C. 154(b) by 312 days.

(21) Appl. No.: 13/298,247

(22) Filed: Nov. 16, 2011

(65) Prior Publication Data

US 2013/0123574 A1   May 16, 2013

(51) Int. Cl.
| | |
|---|---|
| *A61M 39/02* | (2006.01) |
| *A61M 39/04* | (2006.01) |
| *A61F 5/00* | (2006.01) |
| *A61M 39/00* | (2006.01) |

(52) U.S. Cl.
CPC .......... *A61F 5/0056* (2013.01); *A61M 39/0208* (2013.01); *A61M 39/0247* (2013.01); *A61M 39/04* (2013.01); *A61M 2039/0036* (2013.01); *A61M 2039/0072* (2013.01); *A61M 2039/027* (2013.01); *A61M 2039/0223* (2013.01); *A61M 2039/0229* (2013.01); *A61M 2039/0235* (2013.01); *A61M 2039/0255* (2013.01); *A61M 2039/0276* (2013.01); *A61M 2039/0282* (2013.01)

(58) Field of Classification Search
CPC ............ A61M 39/04; A61M 39/0208; A61M 39/0247; A61M 2039/027; A61M 2039/0036; A61M 2039/0072; A61M 2039/0229; A61M 2039/0235; A61M 2039/0255; A61M 2039/0276; A61M 2039/0282
USPC .................. 600/37; 604/175, 288.01–288.04
See application file for complete search history.

(56) References Cited

U.S. PATENT DOCUMENTS

| | | |
|---|---|---|
| 586,113 A | 7/1897 | Bolt |
| 2,163,048 A | 6/1939 | McKee |
| 2,737,954 A | 3/1956 | Knapp |

(Continued)

FOREIGN PATENT DOCUMENTS

| | | |
|---|---|---|
| CN | 1250382 | 4/2000 |
| CN | 1367670 | 9/2002 |

(Continued)

OTHER PUBLICATIONS

Helioscopie Product Insert for Heliogast, pp. 1-11 (undated).

(Continued)

*Primary Examiner* — Charles A Marmor, II
*Assistant Examiner* — Thaddeus Cox
(74) *Attorney, Agent, or Firm* — Gordon & Jacobson, PC

(57) ABSTRACT

Generally described herein are apparatus, systems and methods related to a pre-loaded septum insertable in an access port housing for increasing the control of the compression within the septum and the interference between the septum and the housing. For example, a pair of washers having mating portions may be positioned on respective sides of a rubber septum and bent such that the mating portions of one of the washer are interlocked with the mating portions of the other washer, the interlocked portions forming a tight ring about the septum and generating lateral compression on the septum, thereby "loading" the septum. In addition, fluid seals made of a rubber material with lower durometer than the rubber septum may be used at the interface between the rubber septum and the housing to enhance the fluid sealing functionality while promoting the self-sealing features of the rubber septum.

22 Claims, 5 Drawing Sheets

(56) References Cited

U.S. PATENT DOCUMENTS

| | | | |
|---|---|---|---|
| 3,371,352 | A | 3/1968 | Siposs et al. |
| 3,569,660 | A | 3/1971 | Houldcroft |
| 3,587,115 | A | 6/1971 | Shiley |
| 3,596,660 | A | 8/1971 | Melone |
| 3,667,081 | A | 6/1972 | Burger |
| 3,688,764 | A | 9/1972 | Reed |
| 3,731,352 | A | 5/1973 | Okamoto et al. |
| 3,840,018 | A | 10/1974 | Heifetz |
| 3,958,562 | A | 5/1976 | Hakim et al. |
| 3,971,376 | A | 7/1976 | Wichterle |
| 4,019,499 | A | 4/1977 | Fitzgerald |
| 4,118,805 | A | 10/1978 | Reimels |
| 4,151,835 | A | 5/1979 | Showell et al. |
| 4,161,943 | A | 7/1979 | Nogier |
| 4,164,943 | A | 8/1979 | Hill et al. |
| 4,190,040 | A | 2/1980 | Schulte |
| 4,233,992 | A | 11/1980 | Bisping |
| 4,265,252 | A | 5/1981 | Chubbuck et al. |
| 4,280,722 | A | 7/1981 | Guptil et al. |
| 4,413,985 | A | 11/1983 | Wellner et al. |
| 4,474,572 | A | 10/1984 | McNaughton et al. |
| 4,502,335 | A | 3/1985 | Wamstad et al. |
| 4,543,088 | A | 9/1985 | Bootman et al. |
| 4,557,722 | A | 12/1985 | Harris |
| 4,569,675 | A | 2/1986 | Prosl et al. |
| 4,588,394 | A | 5/1986 | Schulte et al. |
| 4,592,339 | A | 6/1986 | Kuzmak et al. |
| 4,592,355 | A | 6/1986 | Antebi |
| 4,634,427 | A | 1/1987 | Hannula et al. |
| 4,655,765 | A | 4/1987 | Swift |
| 4,673,394 | A | 6/1987 | Fenton, Jr. et al. |
| 4,692,146 | A | 9/1987 | Hilger |
| 4,696,288 | A | 9/1987 | Kuzmak et al. |
| 4,704,103 | A | 11/1987 | Stober et al. |
| 4,710,174 | A | 12/1987 | Moden et al. |
| 4,738,657 | A | 4/1988 | Hancock et al. |
| 4,767,410 | A | 8/1988 | Moden et al. |
| 4,772,270 | A | 9/1988 | Wiita et al. |
| 4,778,452 | A | 10/1988 | Moden et al. |
| 4,781,680 | A | 11/1988 | Redmond et al. |
| 4,796,641 | A | 1/1989 | Mills et al. |
| 4,802,885 | A | 2/1989 | Weeks et al. |
| 4,832,054 | A | 5/1989 | Bark |
| 4,840,615 | A | 6/1989 | Hancock et al. |
| 4,850,227 | A | 7/1989 | Luettgen et al. |
| 4,857,053 | A | 8/1989 | Dalton |
| 4,858,623 | A | 8/1989 | Bradshaw et al. |
| 4,861,341 | A | 8/1989 | Woodburn |
| 4,881,939 | A | 11/1989 | Newman |
| 4,886,501 | A | 12/1989 | Johnston et al. |
| 4,902,278 | A | 2/1990 | Maget et al. |
| 4,904,241 | A | 2/1990 | Bark |
| 4,913,702 | A | 4/1990 | Yum et al. |
| 4,915,690 | A | 4/1990 | Cone et al. |
| 4,929,230 | A | 5/1990 | Pfleger |
| 4,929,236 | A | 5/1990 | Sampson |
| 4,966,588 | A | 10/1990 | Rayman et al. |
| 4,967,755 | A | 11/1990 | Pohndorf |
| 4,978,338 | A | 12/1990 | Melsky et al. |
| 5,006,115 | A | 4/1991 | McDonald |
| 5,013,298 | A | 5/1991 | Moden et al. |
| 5,026,344 | A | 6/1991 | Dijkstra et al. |
| 5,041,098 | A | 8/1991 | Loiterman et al. |
| 5,045,060 | A | 9/1991 | Melsky et al. |
| 5,074,868 | A | 12/1991 | Kuzmak |
| 5,090,954 | A | 2/1992 | Geary |
| 5,092,897 | A | 3/1992 | Forte |
| 5,094,244 | A | 3/1992 | Callahan et al. |
| 5,108,377 | A | 4/1992 | Cone et al. |
| 5,125,408 | A | 6/1992 | Basser |
| 5,133,753 | A | 7/1992 | Bark et al. |
| 5,137,529 | A | 8/1992 | Watson et al. |
| 5,147,483 | A | 9/1992 | Melsky et al. |
| 5,152,747 | A | 10/1992 | Olivier |
| 5,167,638 | A | 12/1992 | Felix et al. |
| 5,185,003 | A | 2/1993 | Brethauer |
| 5,207,644 | A | 5/1993 | Strecker |
| 5,213,574 | A | 5/1993 | Tucker |
| 5,226,429 | A | 7/1993 | Kuzmak |
| 5,226,894 | A | 7/1993 | Haber et al. |
| 5,250,026 | A | 10/1993 | Ehrlich et al. |
| 5,273,537 | A | 12/1993 | Haskvitz et al. |
| 5,281,205 | A | 1/1994 | McPherson |
| 5,284,479 | A | 2/1994 | de Jong |
| 5,318,545 | A | 6/1994 | Tucker |
| 5,336,194 | A | 8/1994 | Polaschegg et al. |
| 5,337,747 | A | 8/1994 | Neftel |
| 5,356,381 | A | 10/1994 | Ensminger et al. |
| 5,360,407 | A | 11/1994 | Leonard et al. |
| 5,368,040 | A | 11/1994 | Carney |
| 5,387,192 | A | 2/1995 | Glantz et al. |
| 5,391,164 | A | 2/1995 | Giampapa |
| 5,449,368 | A | 9/1995 | Kuzmak |
| 5,476,460 | A | 12/1995 | Montalvo |
| 5,514,174 | A | 5/1996 | Heil, Jr. et al. |
| 5,540,648 | A | 7/1996 | Yoon |
| 5,556,388 | A | 9/1996 | Johlin, Jr. |
| 5,558,641 | A | 9/1996 | Glantz et al. |
| 5,562,617 | A | 10/1996 | Finch, Jr. et al. |
| 5,571,104 | A | 11/1996 | Li |
| 5,575,777 | A | 11/1996 | Cover et al. |
| 5,601,604 | A | 2/1997 | Vincent |
| 5,637,102 | A | 6/1997 | Tolkoff et al. |
| 5,653,755 | A | 8/1997 | Ledergerber |
| 5,658,298 | A | 8/1997 | Vincent et al. |
| 5,674,397 | A | 10/1997 | Pawlak et al. |
| 5,683,447 | A | 11/1997 | Bush et al. |
| 5,688,237 | A | 11/1997 | Rozga et al. |
| 5,695,490 | A | 12/1997 | Flaherty et al. |
| 5,716,342 | A | 2/1998 | Dumbraveanu et al. |
| 5,718,682 | A | 2/1998 | Tucker |
| 5,722,957 | A | 3/1998 | Steinbach |
| 5,748,200 | A | 5/1998 | Funahashi |
| 5,810,735 | A | 9/1998 | Halperin et al. |
| 5,814,019 | A | 9/1998 | Steinbach et al. |
| 5,833,654 | A | 11/1998 | Powers et al. |
| 5,843,033 | A | 12/1998 | Ropiak |
| RE36,176 | E | 3/1999 | Kuzmak |
| 5,883,654 | A | 3/1999 | Katsuyama |
| 5,902,598 | A | 5/1999 | Chen et al. |
| 5,906,596 | A | 5/1999 | Tallarida |
| 5,910,149 | A | 6/1999 | Kuzmak |
| 5,911,704 | A | 6/1999 | Humes |
| 5,931,829 | A | 8/1999 | Burbank et al. |
| 5,932,460 | A | 8/1999 | Mills et al. |
| 5,935,083 | A | 8/1999 | Williams |
| 5,938,669 | A | 8/1999 | Klaiber et al. |
| 5,951,512 | A | 9/1999 | Dalton |
| 6,024,704 | A | 2/2000 | Meador et al. |
| 6,030,369 | A | 2/2000 | Engelson et al. |
| 6,039,712 | A | 3/2000 | Fogarty et al. |
| 6,074,341 | A | 6/2000 | Anderson et al. |
| 6,090,066 | A | 7/2000 | Schnell |
| 6,098,405 | A | 8/2000 | Miyata et al. |
| 6,102,678 | A | 8/2000 | Peclat |
| 6,102,922 | A | 8/2000 | Jakobsson et al. |
| 6,123,700 | A | 9/2000 | Mills et al. |
| 6,152,885 | A | 11/2000 | Taepke |
| 6,171,252 | B1 | 1/2001 | Roberts |
| 6,183,449 | B1 | 2/2001 | Sibbitt |
| 6,213,973 | B1 * | 4/2001 | Eliasen et al. ............. 604/93.01 |
| 6,221,024 | B1 | 4/2001 | Miesel |
| 6,234,973 | B1 | 5/2001 | Meador et al. |
| 6,258,079 | B1 | 7/2001 | Burbank et al. |
| 6,264,676 | B1 | 7/2001 | Gellman et al. |
| 6,270,475 | B1 | 8/2001 | Bestetti et al. |
| 6,283,949 | B1 | 9/2001 | Roorda |
| 6,321,124 | B1 | 11/2001 | Cigaina |
| 6,349,740 | B1 | 2/2002 | Cho et al. |
| 6,432,040 | B1 | 8/2002 | Meah |
| 6,450,946 | B1 | 9/2002 | Forsell |
| 6,453,907 | B1 | 9/2002 | Forsell |
| 6,454,699 | B1 | 9/2002 | Forsell |
| 6,459,917 | B1 | 10/2002 | Gowda et al. |

(56) References Cited

U.S. PATENT DOCUMENTS

| | | | |
|---|---|---|---|
| 6,461,293 B1 | 10/2002 | Forsell |
| 6,464,628 B1 | 10/2002 | Forsell |
| 6,470,213 B1 | 10/2002 | Alley |
| 6,470,892 B1 | 10/2002 | Forsell |
| 6,478,783 B1 | 11/2002 | Moorehead |
| 6,511,490 B2 | 1/2003 | Robert |
| 6,547,801 B1 | 4/2003 | Dargent et al. |
| 6,572,587 B2 | 6/2003 | Lerman et al. |
| 6,589,184 B2 | 7/2003 | Noren et al. |
| 6,648,849 B2 | 11/2003 | Tenhuisen et al. |
| 6,666,845 B2 | 12/2003 | Hooper et al. |
| 6,689,100 B2 | 2/2004 | Connelly et al. |
| 6,723,053 B2 | 4/2004 | Ackerman et al. |
| 6,733,519 B2 | 5/2004 | Lashinski et al. |
| 6,792,309 B1 | 9/2004 | Noren |
| 6,810,880 B1 | 11/2004 | Jennings, Jr. et al. |
| 6,813,964 B1 | 11/2004 | Clark et al. |
| 6,860,857 B2 | 3/2005 | Noren et al. |
| 6,915,162 B2 | 7/2005 | Noren et al. |
| 6,921,267 B2 | 7/2005 | van Oostrom et al. |
| 6,929,631 B1 | 8/2005 | Brugger et al. |
| 6,939,299 B1 | 9/2005 | Petersen et al. |
| 6,953,444 B2 | 10/2005 | Rosenberg |
| 6,964,204 B2 | 11/2005 | Clark et al. |
| 6,966,875 B1 | 11/2005 | Longobardi |
| 6,997,914 B2 | 2/2006 | Smith et al. |
| 7,017,583 B2 | 3/2006 | Forsell |
| 7,020,531 B1 | 3/2006 | Colliou et al. |
| 7,056,286 B2 | 6/2006 | Ravenscroft et al. |
| 7,063,669 B2 | 6/2006 | Brawner et al. |
| 7,073,387 B2 | 7/2006 | Zdeblick et al. |
| 7,082,843 B2 | 8/2006 | Clark et al. |
| 7,131,945 B2 | 11/2006 | Fink et al. |
| 7,144,400 B2 | 12/2006 | Byrum et al. |
| 7,149,587 B2 | 12/2006 | Wardle et al. |
| 7,191,007 B2 | 3/2007 | Desai et al. |
| 7,195,774 B2 | 3/2007 | Carvalho et al. |
| 7,223,239 B2 | 5/2007 | Schulze et al. |
| 7,226,419 B2 | 6/2007 | Lane et al. |
| 7,261,003 B2 | 8/2007 | McDonald et al. |
| 7,267,645 B2 | 9/2007 | Anderson et al. |
| 7,282,023 B2 | 10/2007 | Frering |
| 7,311,716 B2 | 12/2007 | Byrum |
| 7,311,717 B2 | 12/2007 | Egle |
| 7,351,198 B2 | 4/2008 | Byrum et al. |
| 7,351,226 B1 | 4/2008 | Herskowitz |
| 7,351,240 B2 | 4/2008 | Hassler, Jr. et al. |
| 7,353,747 B2 | 4/2008 | Swayze et al. |
| 7,364,542 B2 | 4/2008 | Jambor et al. |
| 7,367,937 B2 | 5/2008 | Jambor et al. |
| 7,374,557 B2 | 5/2008 | Conlon et al. |
| 7,374,565 B2 | 5/2008 | Hassler, Jr. et al. |
| 7,390,294 B2 | 6/2008 | Hassler, Jr. |
| 7,413,547 B1 | 8/2008 | Lichtscheidl et al. |
| 7,416,528 B2 | 8/2008 | Crawford et al. |
| 7,437,951 B2 | 10/2008 | McDonald et al. |
| 7,438,718 B2 | 10/2008 | Milliman et al. |
| 7,445,614 B2 | 11/2008 | Bunodiere et al. |
| 7,468,038 B2 | 12/2008 | Ye et al. |
| 7,500,944 B2 | 3/2009 | Byrum et al. |
| 7,510,530 B2 | 3/2009 | Hashimoto et al. |
| 7,530,943 B2 | 5/2009 | Lechner |
| 7,553,298 B2 | 6/2009 | Hunt et al. |
| 7,561,916 B2 | 7/2009 | Hunt et al. |
| 7,580,746 B2 | 8/2009 | Gilkerson et al. |
| 7,591,185 B1 | 9/2009 | Mothilal et al. |
| 7,593,777 B2 | 9/2009 | Gerber |
| 7,634,319 B2 | 12/2009 | Schneider et al. |
| 7,651,483 B2 | 1/2010 | Byrum et al. |
| 7,658,196 B2 | 2/2010 | Ferreri et al. |
| 7,699,770 B2 | 4/2010 | Hassler, Jr. et al. |
| 7,708,722 B2 | 5/2010 | Glenn |
| 7,762,998 B2 | 7/2010 | Birk et al. |
| 7,762,999 B2 | 7/2010 | Byrum |
| 7,775,215 B2 | 8/2010 | Hassler, Jr. et al. |
| 7,775,966 B2 | 8/2010 | Dlugos et al. |
| 7,811,275 B2 | 10/2010 | Birk et al. |
| 7,850,660 B2 | 12/2010 | Uth et al. |
| 7,862,546 B2 | 1/2011 | Conlon et al. |
| 7,909,754 B2 | 3/2011 | Hassler, Jr. et al. |
| 7,909,804 B2 | 3/2011 | Stats |
| 8,007,474 B2 | 8/2011 | Uth et al. |
| 2001/0052141 A1 | 12/2001 | Andersen |
| 2002/0013545 A1 | 1/2002 | Soltanpour et al. |
| 2002/0058969 A1 | 5/2002 | Noren et al. |
| 2002/0087147 A1 | 7/2002 | Hooper et al. |
| 2002/0095181 A1 | 7/2002 | Beyar |
| 2002/0139208 A1 | 10/2002 | Yatskov |
| 2002/0198548 A1 | 12/2002 | Robert |
| 2003/0045800 A1 | 3/2003 | Noren et al. |
| 2003/0045910 A1 | 3/2003 | Sorensen et al. |
| 2003/0073880 A1 | 4/2003 | Polsky et al. |
| 2003/0078506 A1 | 4/2003 | Noren et al. |
| 2003/0139690 A1 | 7/2003 | Aebli et al. |
| 2004/0064110 A1 | 4/2004 | Forsell |
| 2004/0065615 A1 | 4/2004 | Hooper et al. |
| 2004/0068233 A1 | 4/2004 | DiMatteo |
| 2004/0082908 A1 | 4/2004 | Whitehurst et al. |
| 2004/0111050 A1 | 6/2004 | Smedley et al. |
| 2004/0204692 A1 | 10/2004 | Eliasen |
| 2004/0254536 A1 | 12/2004 | Conlon et al. |
| 2004/0254537 A1 | 12/2004 | Conlon et al. |
| 2004/0260229 A1 | 12/2004 | Meir |
| 2004/0260319 A1 | 12/2004 | Egle |
| 2004/0267288 A1 | 12/2004 | Byrum et al. |
| 2004/0267291 A1 | 12/2004 | Byrum et al. |
| 2004/0267292 A1 | 12/2004 | Byrum et al. |
| 2004/0267293 A1 | 12/2004 | Byrum et al. |
| 2004/0267377 A1 | 12/2004 | Egle |
| 2005/0010177 A1 | 1/2005 | Tsai |
| 2005/0045060 A1 | 3/2005 | Forbes et al. |
| 2005/0049578 A1 | 3/2005 | Tu et al. |
| 2005/0070875 A1 | 3/2005 | Kulessa |
| 2005/0070937 A1 | 3/2005 | Jambor et al. |
| 2005/0085778 A1 | 4/2005 | Parks |
| 2005/0092093 A1 | 5/2005 | Kang et al. |
| 2005/0131325 A1 | 6/2005 | Chen et al. |
| 2005/0131352 A1 | 6/2005 | Conlon et al. |
| 2005/0131383 A1 | 6/2005 | Chen et al. |
| 2005/0148956 A1 | 7/2005 | Conlon et al. |
| 2005/0149143 A1 | 7/2005 | Libbus et al. |
| 2005/0209573 A1 | 9/2005 | Brugger et al. |
| 2005/0240155 A1 | 10/2005 | Conlon |
| 2005/0240156 A1 | 10/2005 | Conlon |
| 2005/0267500 A1 | 12/2005 | Hassler, Jr. et al. |
| 2005/0277899 A1 | 12/2005 | Conlon et al. |
| 2005/0283041 A1 | 12/2005 | Egle |
| 2005/0283118 A1 | 12/2005 | Uth et al. |
| 2005/0283119 A1 | 12/2005 | Uth et al. |
| 2006/0074439 A1 | 4/2006 | Garner et al. |
| 2006/0122578 A1 | 6/2006 | Lord et al. |
| 2006/0161186 A1 | 7/2006 | Hassler et al. |
| 2006/0173423 A1 | 8/2006 | Conlon |
| 2006/0173424 A1 | 8/2006 | Conlon |
| 2006/0178647 A1 | 8/2006 | Stats |
| 2006/0178648 A1 | 8/2006 | Barron et al. |
| 2006/0184141 A1 | 8/2006 | Smith et al. |
| 2006/0189887 A1 | 8/2006 | Hassler, Jr. et al. |
| 2006/0189888 A1 | 8/2006 | Hassler, Jr. et al. |
| 2006/0190039 A1 | 8/2006 | Birk et al. |
| 2006/0199997 A1 | 9/2006 | Hassler, Jr. et al. |
| 2006/0211912 A1 | 9/2006 | Dlugos et al. |
| 2006/0211913 A1 | 9/2006 | Dlugos et al. |
| 2006/0211914 A1 | 9/2006 | Hassler, Jr. et al. |
| 2006/0217668 A1 | 9/2006 | Schulze et al. |
| 2006/0217673 A1 | 9/2006 | Schulze et al. |
| 2006/0235445 A1 | 10/2006 | Birk et al. |
| 2006/0235448 A1 | 10/2006 | Roslin et al. |
| 2006/0247539 A1 | 11/2006 | Schugt et al. |
| 2006/0264898 A1* | 11/2006 | Beasley et al. ............ 604/506 |
| 2006/0266128 A1 | 11/2006 | Clark et al. |
| 2006/0293625 A1 | 12/2006 | Hunt et al. |
| 2006/0293626 A1 | 12/2006 | Byrum et al. |
| 2006/0293627 A1 | 12/2006 | Byrum et al. |

(56) References Cited

U.S. PATENT DOCUMENTS

| | | |
|---|---|---|
| 2006/0293628 A1 | 12/2006 | Hunt et al. |
| 2007/0010790 A1 | 1/2007 | Byrum et al. |
| 2007/0015954 A1 | 1/2007 | Dlugos |
| 2007/0015955 A1 | 1/2007 | Tsonton |
| 2007/0016231 A1 | 1/2007 | Jambor et al. |
| 2007/0027356 A1 | 2/2007 | Ortiz |
| 2007/0038255 A1 | 2/2007 | Kieval et al. |
| 2007/0060959 A1 | 3/2007 | Salo et al. |
| 2007/0073250 A1 | 3/2007 | Schneiter |
| 2007/0078391 A1 | 4/2007 | Wortley et al. |
| 2007/0088336 A1 | 4/2007 | Dalton |
| 2007/0088391 A1 | 4/2007 | McAlexander et al. |
| 2007/0129765 A1 | 6/2007 | Gilkerson et al. |
| 2007/0135758 A1 | 6/2007 | Childers et al. |
| 2007/0149947 A1 | 6/2007 | Byrum |
| 2007/0156013 A1 | 7/2007 | Birk |
| 2007/0158769 A1 | 7/2007 | You |
| 2007/0161958 A1 | 7/2007 | Glenn |
| 2007/0167672 A1 | 7/2007 | Dlugos et al. |
| 2007/0173685 A1 | 7/2007 | Jambor et al. |
| 2007/0185455 A1* | 8/2007 | Fangrow, Jr. ............ 604/164.01 |
| 2007/0185462 A1 | 8/2007 | Byrum |
| 2007/0191717 A1 | 8/2007 | Rosen et al. |
| 2007/0205384 A1 | 9/2007 | Kurosawa |
| 2007/0208313 A1 | 9/2007 | Conlon et al. |
| 2007/0213837 A1 | 9/2007 | Ferreri et al. |
| 2007/0219510 A1 | 9/2007 | Zinn et al. |
| 2007/0235083 A1 | 10/2007 | Dlugos |
| 2007/0250086 A1 | 10/2007 | Wiley et al. |
| 2007/0255165 A1 | 11/2007 | Uesugi et al. |
| 2007/0255234 A1 | 11/2007 | Haase et al. |
| 2007/0265666 A1 | 11/2007 | Roberts et al. |
| 2007/0282196 A1 | 12/2007 | Birk et al. |
| 2007/0282308 A1* | 12/2007 | Bell ............................ 604/539 |
| 2007/0293829 A1 | 12/2007 | Conlon et al. |
| 2008/0009680 A1 | 1/2008 | Hassler, Jr. |
| 2008/0015406 A1 | 1/2008 | Dlugos et al. |
| 2008/0039772 A1 | 2/2008 | Chantriaux et al. |
| 2008/0058632 A1 | 3/2008 | Tai et al. |
| 2008/0097496 A1 | 4/2008 | Chang et al. |
| 2008/0114308 A1 | 5/2008 | di Palma et al. |
| 2008/0119798 A1 | 5/2008 | Chantriaux et al. |
| 2008/0243093 A1 | 10/2008 | Kalpin et al. |
| 2008/0249806 A1 | 10/2008 | Dlugos et al. |
| 2008/0250340 A1 | 10/2008 | Dlugos et al. |
| 2008/0250341 A1 | 10/2008 | Dlugos et al. |
| 2008/0255403 A1 | 10/2008 | Voegele et al. |
| 2008/0255414 A1 | 10/2008 | Voegele et al. |
| 2008/0255425 A1 | 10/2008 | Voegele et al. |
| 2008/0255459 A1 | 10/2008 | Voegele et al. |
| 2008/0255537 A1 | 10/2008 | Voegele et al. |
| 2008/0281412 A1 | 11/2008 | Smith et al. |
| 2008/0287969 A1 | 11/2008 | Tsonton et al. |
| 2008/0287974 A1 | 11/2008 | Widenhouse et al. |
| 2008/0312553 A1 | 12/2008 | Timmons |
| 2008/0319435 A1 | 12/2008 | Rioux et al. |
| 2009/0018608 A1 | 1/2009 | Schwartz et al. |
| 2009/0048524 A1 | 2/2009 | Wildau et al. |
| 2009/0054914 A1 | 2/2009 | Lechner |
| 2009/0062825 A1 | 3/2009 | Pool et al. |
| 2009/0071258 A1 | 3/2009 | Kouda et al. |
| 2009/0076466 A1 | 3/2009 | Quebbemann et al. |
| 2009/0082757 A1 | 3/2009 | Rogers et al. |
| 2009/0082793 A1 | 3/2009 | Birk |
| 2009/0093768 A1 | 4/2009 | Conlon et al. |
| 2009/0099538 A1 | 4/2009 | Paganon |
| 2009/0105735 A1 | 4/2009 | Stam et al. |
| 2009/0112308 A1 | 4/2009 | Kassem |
| 2009/0118572 A1 | 5/2009 | Lechner |
| 2009/0149874 A1 | 6/2009 | Ortiz et al. |
| 2009/0157106 A1 | 6/2009 | Marcotte et al. |
| 2009/0157107 A1 | 6/2009 | Kierath et al. |
| 2009/0157113 A1 | 6/2009 | Marcotte et al. |
| 2009/0171375 A1 | 7/2009 | Coe et al. |
| 2009/0171378 A1 | 7/2009 | Coe et al. |
| 2009/0171379 A1 | 7/2009 | Coe et al. |
| 2009/0192404 A1 | 7/2009 | Ortiz et al. |
| 2009/0192415 A1 | 7/2009 | Ortiz et al. |
| 2009/0192533 A1 | 7/2009 | Dlugos, Jr. et al. |
| 2009/0192534 A1 | 7/2009 | Ortiz et al. |
| 2009/0192541 A1 | 7/2009 | Ortiz et al. |
| 2009/0198261 A1 | 8/2009 | Schweikert |
| 2009/0202387 A1 | 8/2009 | Dlugos, Jr. et al. |
| 2009/0204131 A1 | 8/2009 | Ortiz et al. |
| 2009/0204132 A1 | 8/2009 | Ortiz et al. |
| 2009/0209995 A1 | 8/2009 | Byrum et al. |
| 2009/0216255 A1 | 8/2009 | Coe et al. |
| 2009/0221974 A1 | 9/2009 | Paganon |
| 2009/0222031 A1 | 9/2009 | Axelsson |
| 2009/0222065 A1 | 9/2009 | Dlugos, Jr. et al. |
| 2009/0227862 A1 | 9/2009 | Smith et al. |
| 2009/0228028 A1 | 9/2009 | Coe et al. |
| 2009/0228072 A1 | 9/2009 | Coe et al. |
| 2009/0248125 A1 | 10/2009 | Brostrom |
| 2009/0248126 A1 | 10/2009 | Nippoldt et al. |
| 2009/0254052 A1 | 10/2009 | Birk et al. |
| 2009/0259190 A1 | 10/2009 | Birk et al. |
| 2009/0259191 A1 | 10/2009 | Birk et al. |
| 2009/0259231 A1 | 10/2009 | Birk et al. |
| 2009/0264901 A1 | 10/2009 | Franklin et al. |
| 2009/0270904 A1 | 10/2009 | Birk et al. |
| 2009/0299216 A1 | 12/2009 | Chen et al. |
| 2009/0299672 A1 | 12/2009 | Zhang et al. |
| 2009/0306462 A1 | 12/2009 | Lechner |
| 2009/0308169 A1 | 12/2009 | Mothilal et al. |
| 2010/0087843 A1 | 4/2010 | Bertolote et al. |
| 2010/0100079 A1 | 4/2010 | Berkcan et al. |
| 2010/0114149 A1 | 5/2010 | Albrecht et al. |
| 2010/0130941 A1 | 5/2010 | Conlon et al. |
| 2010/0152532 A1 | 6/2010 | Marcotte |
| 2010/0191271 A1 | 7/2010 | Lau et al. |
| 2010/0211085 A1 | 8/2010 | Uth et al. |
| 2010/0217198 A1 | 8/2010 | Franklin et al. |
| 2010/0217199 A1 | 8/2010 | Uth et al. |
| 2010/0217200 A1 | 8/2010 | Uth et al. |
| 2010/0228080 A1 | 9/2010 | Tavori et al. |
| 2010/0234808 A1 | 9/2010 | Uth et al. |
| 2011/0054407 A1 | 3/2011 | Olroyd et al. |
| 2011/0082426 A1 | 4/2011 | Conlon et al. |
| 2011/0270019 A1* | 11/2011 | Deuel et al. .................. 600/37 |

FOREIGN PATENT DOCUMENTS

| | | |
|---|---|---|
| DE | 3927001 | 2/1991 |
| DE | 4211045 | 10/1993 |
| DE | 19751791 | 5/1997 |
| DE | 19745654 | 4/1999 |
| EP | 0343910 | 11/1989 |
| EP | 0611561 | 9/1993 |
| EP | 0858814 | 8/1998 |
| EP | 0867197 | 9/1998 |
| EP | 1057457 | 12/2000 |
| EP | 1346753 | 9/2003 |
| EP | 1396242 | 3/2004 |
| EP | 1396243 | 3/2004 |
| EP | 1488824 | 12/2004 |
| EP | 1543861 | 6/2005 |
| EP | 1547643 | 6/2005 |
| EP | 1591140 | 11/2005 |
| EP | 1736194 | 12/2006 |
| EP | 1736195 | 12/2006 |
| EP | 1736196 | 12/2006 |
| EP | 1736197 | 12/2006 |
| EP | 1736198 | 12/2006 |
| EP | 1736199 | 12/2006 |
| EP | 1870126 | 12/2007 |
| EP | 1985263 | 10/2008 |
| EP | 2070494 | 6/2009 |
| EP | 2095798 | 9/2009 |
| FR | 2740977 | 5/1997 |
| FR | 2797181 | 2/2001 |
| FR | 2823663 | 10/2002 |
| FR | 2851168 | 8/2004 |
| FR | 2855744 | 12/2004 |

(56) References Cited

FOREIGN PATENT DOCUMENTS

| | | |
|---|---|---|
| FR | 2916980 | 12/2008 |
| FR | 2958170 | 10/2011 |
| JP | 2119877 | 5/1990 |
| JP | 8107934 | 4/1996 |
| SU | 1823791 | 6/1991 |
| WO | WO 92/20519 | 11/1992 |
| WO | WO 94/22520 | 10/1994 |
| WO | WO 96/40357 | 12/1996 |
| WO | WO 97/01370 | 1/1997 |
| WO | WO 99/20338 | 4/1999 |
| WO | WO 99/26543 | 6/1999 |
| WO | WO 99/34859 | 7/1999 |
| WO | WO 00/15158 | 3/2000 |
| WO | WO 00/33901 | 6/2000 |
| WO | WO 01/10359 | 2/2001 |
| WO | WO 01/49245 | 7/2001 |
| WO | WO 01/80926 | 11/2001 |
| WO | WO 01/95813 | 12/2001 |
| WO | WO 02/10667 | 2/2002 |
| WO | WO 02/074381 | 9/2002 |
| WO | WO 03/105732 | 12/2003 |
| WO | WO 2004/016971 | 3/2004 |
| WO | WO 2005/037055 | 4/2005 |
| WO | WO 2005/072627 | 8/2005 |
| WO | WO 2006/021695 | 3/2006 |
| WO | WO 2009/007526 | 1/2009 |
| WO | WO 2009/129474 | 10/2009 |

OTHER PUBLICATIONS

Autumn K. et al.; "Evidence of Van Der Waals Adhesion in Gecko Setae"; PNAS; vol. 99; No. 19; pp. 12252-12256; Sep. 17, 2012.

Geim AK. et al.; "Microfabricated Adhesive Mimicking Gecko Foot-Hair"; Nature Materials Abstract only; vol. 2; No. 7; 2003.

Yamagami, Takuji; "Technical Developments: Use of Targeting Guide Wire in Left Subclavian Puncture During Percutaneous Implantation of Port-Catheter Systems Using the Catheter Tip Fixation Method" European Radiology; vol. 13; pp. 863-866; 2003.

Yurdumakan B., et al.; "Synthetic Gecko Foot-Hairs from Multiwalled Carbon Nanotubes"; The Royal Society of Chemistry; p. 3799-3801; 2005.

http://en/wilcipedia.org/Injection_Molding.

* cited by examiner

PRE-LOADED SEPTUM FOR USE WITH AN ACCESS PORT

FIELD

The present invention generally relates to medical systems, devices and uses thereof for treating obesity and/or obesity-related diseases and more specifically relates to a pre-loaded septum for an access port used as a part of a gastric banding system implantable in a patient.

BACKGROUND

Adjustable gastric banding apparatus have provided an effective and substantially less invasive alternative to gastric bypass surgery and other conventional surgical weight loss procedures. Despite the positive outcomes of invasive weight loss procedures, such as gastric bypass surgery, it has been recognized that sustained weight loss can be achieved through a laparoscopically-placed gastric band, for example, the LAP-BAND® (Allergan, Inc., Irvine, Calif.) gastric band or the LAP-BAND AP® (Allergan, Inc., Irvine, Calif.) gastric band. Generally, gastric bands are placed about the cardia, or upper portion, of a patient's stomach forming a stoma that restricts the food's passage into a lower portion of the stomach. When the stoma is of an appropriate size that is restricted by a gastric band, food held in the upper portion of the stomach may provide a feeling of satiety or fullness that discourages overeating. Unlike gastric bypass procedures, gastric band apparatus are reversible and require no permanent modification to the gastrointestinal tract. An example of a gastric banding system is disclosed in Roslin, et al., U.S. Patent Pub. No. 2006/0235448, the entire disclosure of which is incorporated herein by this specific reference.

Over time, a stoma created by a gastric band may need adjustment in order to maintain an appropriate size, which is neither too restrictive nor too passive. Accordingly, prior art gastric band systems provide a subcutaneous fluid access port ("access port") connected to an expandable or inflatable portion of the gastric band. By adding fluid to or removing fluid from the inflatable portion by means of a hypodermic needle inserted into the access port, the effective size of the gastric band can be adjusted to provide a tighter or looser constriction.

Typically, the access port contains a rubber septum while the rest of the access port (e.g., housing) is constructed out of a hard plastic or metal material. The rubber septum is penetrated by the hypodermic needle to add or remove the fluid. However, after the hypodermic needle is removed, the hole created cannot be allowed to cause a leak. Therefore, the rubber septum should have a self-sealing function and "heal" the hole to prevent a leak after the hypodermic needle is removed.

Certain access ports currently in use are designed to withstand tens to hundreds of punctures by utilizing an interference fit between a cavity defined by two or more mating parts of the access port housing and a rubber septum which is initially larger than the cavity, as illustrated in FIG. 1A. FIG. 1B is a cross-sectional view of another prior art access port, which reveals a fluid reservoir or cavity 130 between a septum 135 and the inside walls of a housing 140. The interference fit 160 between the septum 135 and the access port housing 140 serves two functions: (1) to create a fluid seal at the interface between the septum 135 and the access port housing 140; and (2) to provide compression on the septum 135 which helps to ensure self-sealing after a needle punctures the septum 135. However, one drawback of these access ports is the difficulty in controlling the amount of interference with the rubber septum while concurrently ensuring that the housing parts are effectively assembled together (e.g., either by a press fit or ultrasonic welding, etc.). Because these access port designs rely on the interference created solely by the fit between the septum and the housing, these access ports are forced to use the same rubber durometer to accomplish both the fluid seal function and the self-sealing function. However, using the same rubber durometer for both functions is not optimal because the self-sealing function is more effectively accomplished with a higher durometer rubber (since a harder material more effectively returns to its compressed state under compression), and the fluid seal is better achieved with a lower durometer rubber (since a tighter seal is achieved when the rubber is more easily conformable to the housing). In other words, the use of a higher durometer rubber to promote the septum's self-sealing function compromises the effectiveness of the fluid seal, and conversely, the use of a lower durometer rubber to enhance the fluid seal will limit the septum's ability to self-seal.

What is needed is an access port that allows optimization of the fluid seal function through the use of a better suited rubber material while ensuring that the interference created between the housing and the septum does not adversely affect the self-sealing functionality of the septum.

SUMMARY

Generally described herein are apparatus, systems and methods related to a preloaded septum insertable in an access port housing for increasing the control of the interference with the septum and the housing.

In one embodiment, a pair of washers having mating portions may be positioned on respective sides of a rubber septum and bent such that the mating portions of one of the washer are interlocked with the mating portions of the other washer, the interlocked portions forming a tight ring about the septum and generating lateral compression on the septum, thereby "loading" the septum.

In one embodiment, provided is a compressed septum for insertion into an access port housing of a gastric band for the treatment of obesity. The pre-loaded septum includes a septum including a first side and a second side, a top ring having a first set of radially extending mating members positioned on the first side of the septum, and defining a cavity at the center portion of the top ring, and a bottom ring having a second set of radially extending mating members positioned on the second side of the septum, and defining a cavity at the center portion of the bottom ring, wherein the second set of radially extending mating members of the bottom ring is configured to engage the first set of radially extending mating members of the top ring and cause the septum to be compressed such that the first side of the septum protrudes through the cavity of the top ring when the second set of radially extending mating members of the bottom ring and the first set of radially extending mating members of the top ring are manipulated to interlock.

In one embodiment, provided is a pre-loaded septum for insertion into an access port housing of a gastric band for the treatment of obesity. The pre-loaded septum includes a septum including a first side and a second side, a first washer-shaped titanium metal sheet positioned on the first side of the septum, the first washer-shaped titanium metal sheet defining a cavity at the center portion of the first washer-shaped titanium metal sheet, the first washer-shaped titanium metal sheet further including a first set of radially-extending mating members, and a second washer-shaped titanium metal sheet positioned on the second side of the septum, the second washer-shaped titanium metal sheet defining a cavity at the center portion of the second washer-shaped titanium metal sheet, the second washer-shaped titanium metal sheet further including a second set of radially-extending mating members configured to interlock the first set of radially-extending mating members.

In one embodiment, a top compressing layer defining a cavity at the center portion of the compressing layer and having radially-extending mating members may be positioned on a top side of a rubber septum such that the radially-extending mating members extend beyond the edge of the rubber septum. A bottom compressing layer defining a cavity at the center portion of the compressing layer and having radially-extending mating members may be positioned at a bottom side of the rubber septum such that the radially extending mating members of the bottom compressing layer extend beyond the edge of the rubber septum. When the top compressing layer and the bottom compressing layer are positioned as described, the mating members of the top compressing layer and the bottom compressing layer may be manipulated or bent towards each other to contact a side portion of the rubber septum and engage each other. In other words, a mating member of the top compressing layer will engage a corresponding mating member of the bottom compressing layer to form a tight ring about the septum and generate lateral compression on the septum, thereby "loading" the septum and causing the septum to protrude out of the cavity of the top compressing layer and the bottom compressing layer.

In one embodiment, the fluid seals used at the interface between the rubber septum and the housing may be made of a rubber material with lower durometer to enhance the sealing functionality while promoting the self-sealing features of the rubber septum.

BRIEF DESCRIPTION OF THE DRAWINGS

The features, obstacles, and advantages of the present invention will become more apparent from the detailed description set forth below when taken in conjunction with the drawings, wherein.

DETAILED DESCRIPTION

Apparatuses, systems and/or methods that implement the embodiments of the various features of the present invention will now be described with reference to the drawings. The drawings and the associated descriptions are provided to illustrate some embodiments of the present invention and not to limit the scope of the present invention. Throughout the drawings, reference numbers are re-used to indicate correspondence between referenced elements.

Figure 1A:
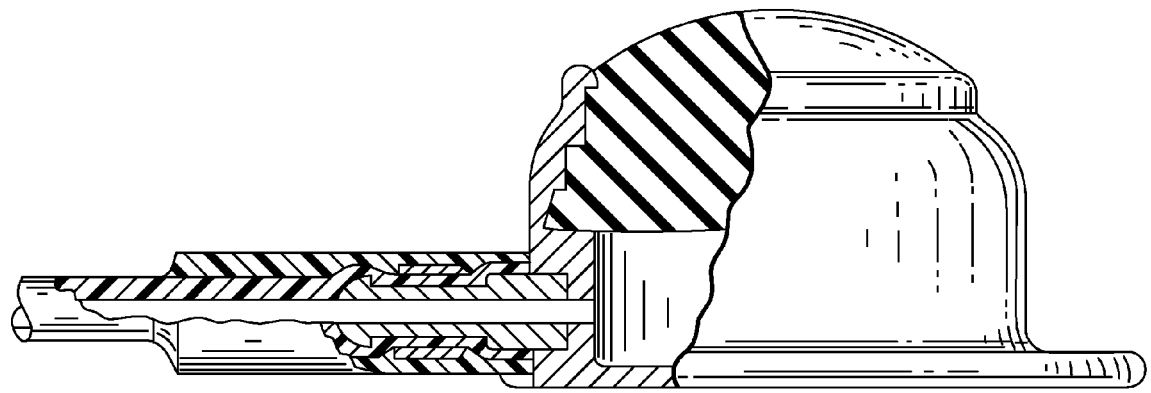
FIG. 1A illustrates a prior art access port.
Figure 1B:
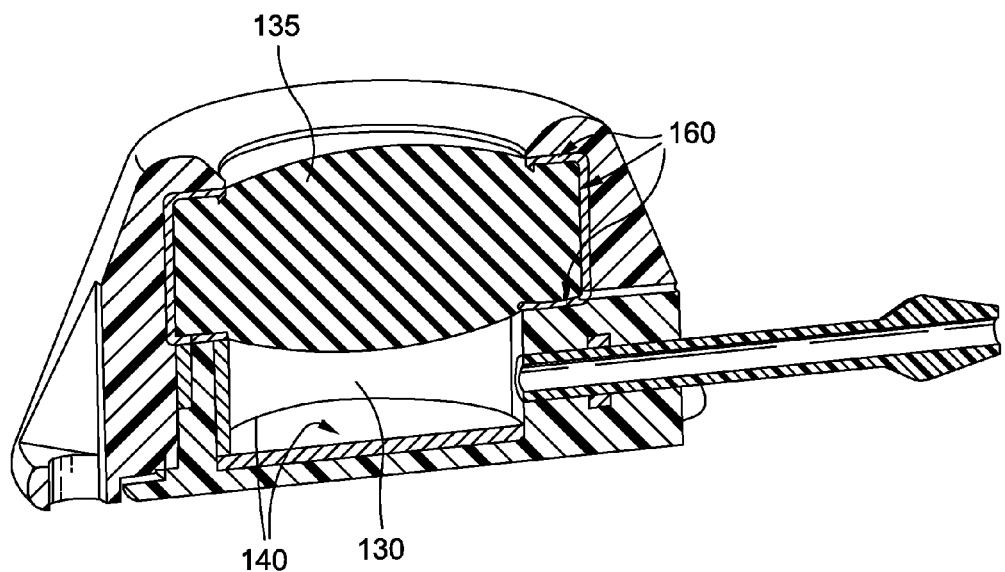
FIG. 1B illustrates a prior art access port.
Figure 2:
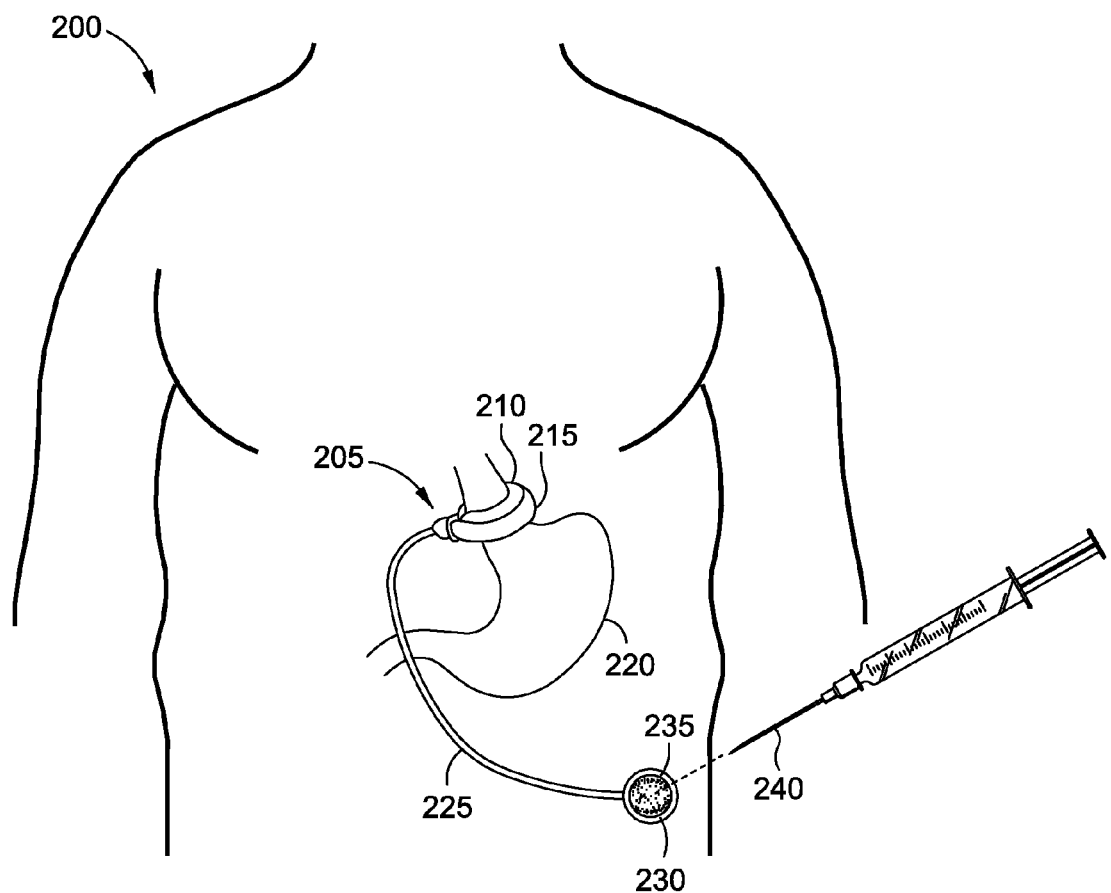
FIG. 2 illustrates a gastric banding system including an access port according to an embodiment of the present invention.

Turning to FIG. 2, a body of a patient 200 having a stomach 220 is illustrated. As shown, a gastric banding system 205 may be positioned within the patient 200, forming a constriction about the upper portion of the stomach 220 via a gastric band 210, and more particularly, via an inflatable portion 215 of the gastric band 210. The gastric band 210 may be connected to an access port 230 by means of a connection tube 225. A hypodermic needle 240 may penetrate the skin of the patient 200 and puncture a septum 235 of the access port 230 to add fluid to or remove fluid from the inflatable portion 215 of the gastric band 210.

One embodiment of the present invention generally provides a pre-loaded septum as related to gastric banding systems, for example, for treatment of obesity and obesity related conditions.

A pre-loaded septum may be compressed and may fit into an access port housing to allow self-sealing properties after a puncture regardless of the amount of interference with the access port housing. The compression on the septum is caused by the top layer or ring and the bottom layer or ring applying a relatively constant pressure on the septum resulting in the septum protruding through the openings in the top layer or ring and the bottom layer or ring. The access port housing may also include a separate washer to act as a fluid seal (of the same or different material as the septum and/or the ring about the septum) for better optimization of the fluid seal function. Such advantages will further be evident as described in conjunction with the figures.

Figure 3:
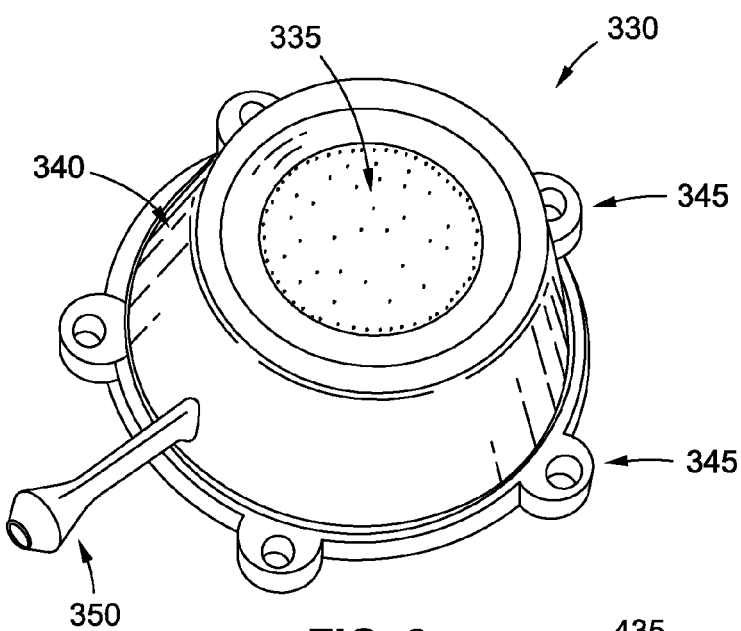
FIG. 3 illustrates an access port according to an embodiment of the present invention.

Turning to FIG. 3, an access port 330 (or injection port) is illustrated with the rest of the gastric banding system omitted for clarity. The access port 330 may be the access port 230 of FIG. 2 and includes a septum 335, a housing 340, suture points 345 and an interface or port 350 for establishing fluid communication with a connection tube (e.g., connection tube 225 of FIG. 2).

Figure 4A:
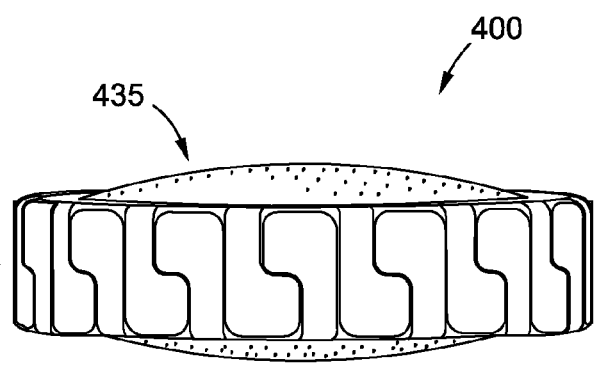
FIG. 4A illustrates a side view of a ring about the septum generating lateral compression on the septum, thereby "loading" the septum according to an embodiment of the present invention.

FIG. 4A illustrates a pre-loaded septum 400 according to an embodiment of the present invention. Here, the pre-loaded septum 400 is illustrated with the housing and fluid seals omitted for clarity. The pre-loaded septum 400 generally fits within the housing. As shown, the pre-loaded septum 400 may include a ring 410 laterally compressing a septum 435, causing the septum 435 to bulge axially. The ring 410 is shown to include a pattern of interlocking "L" shaped fingers.

Figure 4B:
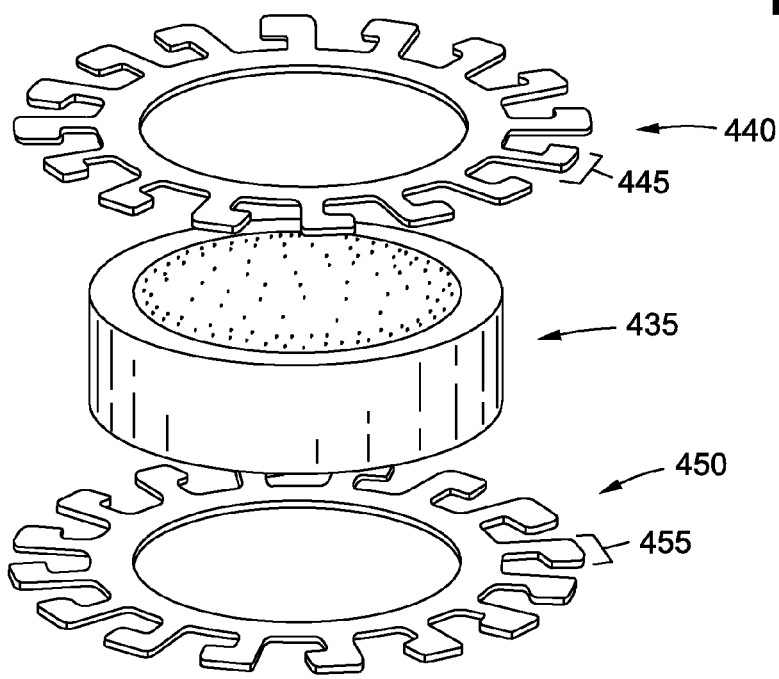
FIG. 4B illustrates an exploded, perspective view of a pair of washers positioned on both sides of a septum according to an embodiment of the present invention.
Figure 4C:
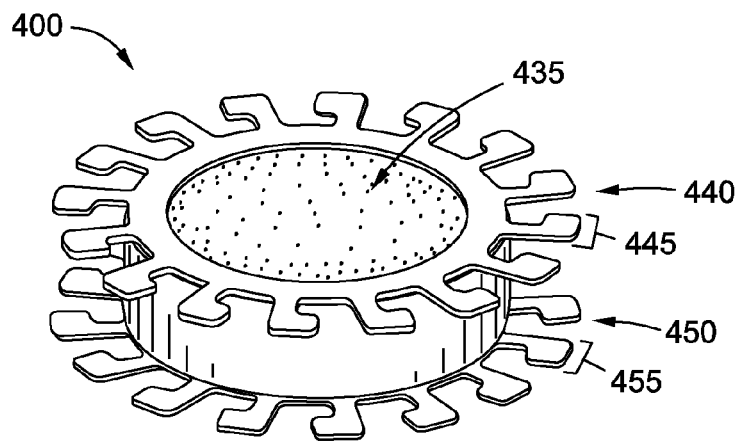
FIG. 4C illustrates a perspective view of the pair of washers of FIG. 4B positioned on both sides of a septum before the engaging members of the washers are engaged according to an embodiment of the present invention.
Figure 4D:
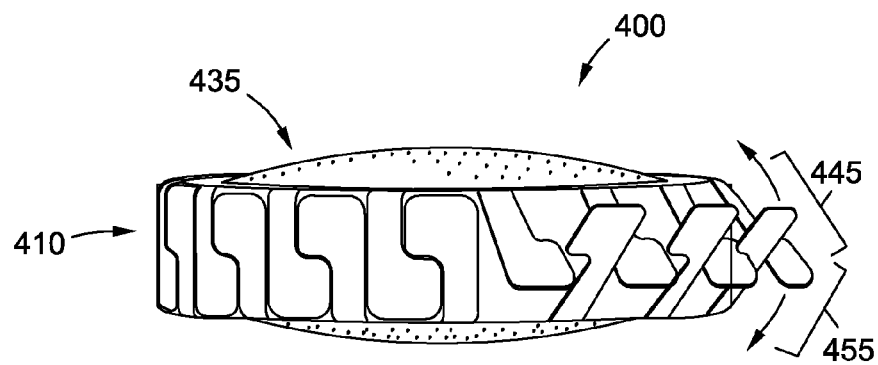
FIG. 4D illustrates a side view of the pair of washers of FIG. 4B with respective engaging members engaging to form a ring about the septum according to an embodiment of the present invention.

FIGS. 4B-4D illustrate how the pre-loaded septum is constructed and the components that make up the pre-loaded septum.

FIG. 4B is an exploded view of the components of the pre-loaded septum 400. Two washer-shaped discs each having a plurality of "L" shaped fingers that may be positioned on the two sides of the septum 435.

More particularly, one of the washer-shaped discs may be a top compressing layer 440 having an inner ring defining a cavity at the center portion of the top compressing layer 440. The top compressing layer 440 may have "L" shaped fingers radially-extending from the inner ring serving as top mating members 445. The top compressing layer 440 may be positioned on a top side of the septum 435 such that the top mating members 445 extend beyond an outer edge of the septum 435.

Analogously, the other washer-shaped disc may be a bottom compressing layer 450 having an inner ring defining a cavity at the center portion of the bottom compressing layer 450. The bottom compressing layer 450 may have "L" shaped fingers radially-extending from the inner ring serving as bottom mating members 455. The bottom compressing layer 450 may be positioned on a bottom side of the septum 435 such that the bottom mating members 455 extend beyond an outer edge of the septum 435.

The top compressing layer 440 and the bottom compressing layer 450, in one embodiment, may be constructed as a thin, metal (e.g., titanium or stainless steel), washer-shaped part. However, other metals may also be used. In addition, certain non-metals, such as PEEK or Polysufone (or other thermoplastics) may be used when sufficient heat is associated with the bending process. The thermoplastic washer can retain its shape upon cooling.

The top compressing layer 440 and the bottom compressing layer 450 may be stamped by a progressive die, laser cut, water-jet cut, machined or blanked to form the desired pattern, for instance, such that the inner ring has a plurality of "L" shaped fingers to serve as the mating members. The top compressing layer 440 and the bottom compressing layer 450 may have a variety of different shaped fingers or interlocking members.

FIG. 4C illustrates the top compressing layer 440 and the bottom compressing layer 450 positioned as described, just prior to compression of the septum 435. Thereafter, the top mating members 445 of the top compressing layer 440 and the bottom mating members 455 of the bottom compressing layer 450 may be manipulated or bent towards each other as illustrated in FIG. 4D to interlock with one another. As the mating members are bent substantially to a 90° angle with respect to its original position, the mating members may contact a side portion of the septum 435. Each mating member of the top compressing layer 440 may engage a corresponding mating member of the bottom compressing layer 450 to form a tight ring 410 about the septum 435 and generate lateral compression on the septum 435, thereby "loading" the septum 435 and causing the septum 435 to protrude out of the cavity of the top compressing layer 440 and the bottom compressing layer 450, as previously shown in FIG. 4A.

Figure 4E:
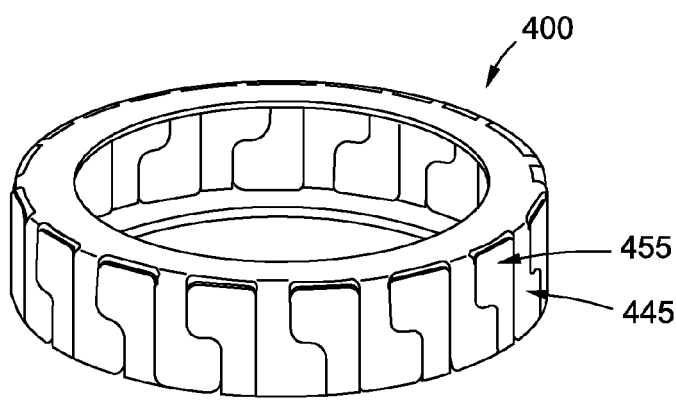
FIG. 4E illustrates a perspective view of the pair of washers of FIG. 4B with respective engaging members fully engaged but without the septum (removed for clarity) according to an embodiment of the present invention.

FIG. 4E illustrates how the ring 410 may appear when the top mating members 445 and the bottom mating members 455 are fully interlocked. At this point, the septum 435 is self-sealing because it is under lateral compression exerted by the ring 410, irrespective of the design of the access port housing.

Figure 5:
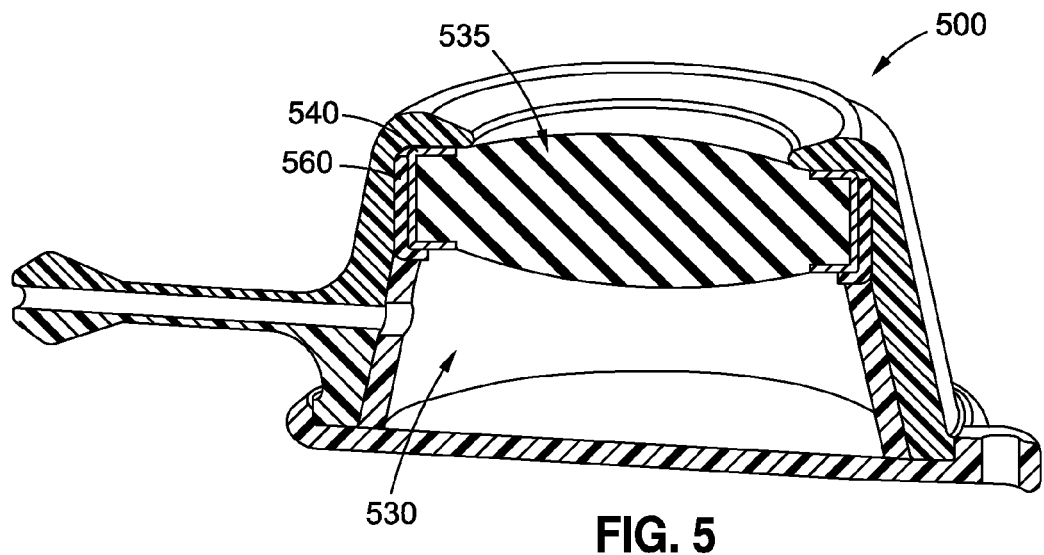
FIG. 5 illustrates a cross-sectional view of the access port, the septum under lateral compression exerted by the ring, and a washer to ensure a fluid seal according to an embodiment of the present invention.

FIG. 5 illustrates a cross-sectional view of an access port 500 utilizing the pre-loaded septum 400 (shown as 535) of FIG. 4D. A fluid seal (or washer) 560 may be positioned at the interface between the pre-loaded septum 535 and a housing 540 to ensure that fluid within a fluid reservoir 530 does not leak out of the housing 540 through the interface. The fluid seal 560 may be constructed out of a rubber with a relatively lower durometer that is better suited for preventing leakage, while the septum 535 may be constructed out of a rubber with a relatively higher durometer. By varying the materials, and in particular, the durometer of the two materials, the self-sealing functionality of the septum 535 may be maximized while also enhancing the sealing functionality provided by the fluid seal 560.

Figure 6A:
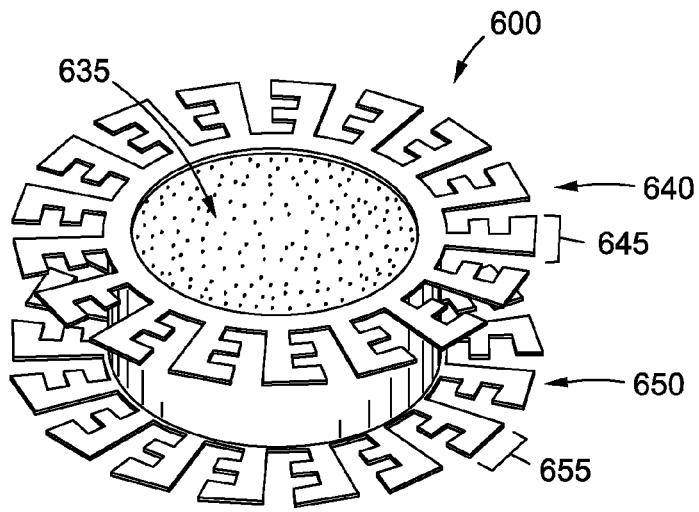
FIG. 6A illustrates an exploded, perspective view of a pair of washers positioned on both sides of a septum according to an embodiment of the present invention.

FIG. 6A illustrates another embodiment of a pre-loaded septum 600 having a different pattern for the interlocking members. Here, an "F-shaped" pattern may serve as top mating members 645 of a top compressing layer 640 while a similar "F-shaped" pattern may serve as bottom mating members 655 of a bottom compressing layer 650. The two F-shaped patterns bend towards each other and come together to form a cohesive ring about the exterior of a septum to compress the septum. More particularly, the F-shaped patterns of the top mating member 645 pair with the corresponding (inverted) F-shaped patterns of the bottom mating member 655 interlock thereby causing compression on the septum.

Figure 6B:
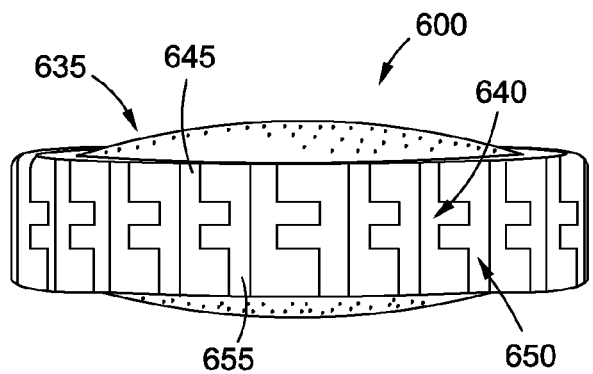
FIG. 6B illustrates a side view of the pair of washers of FIG. 4C with respective engaging members engaged to form a ring about the septum according to an embodiment of the present invention.

FIG. 6B illustrates how the pre-loaded septum 600 of FIG. 6A may appear when compressing a septum 635.

Certain embodiments have been disclosed to clarify the concepts including the above structural configurations. However, one skilled in the art will recognize that an endless number of different patterns (e.g., T-shaped patterns) may be used to construct the ring causing the compression against the septum to result in a pre-loaded septum. Accordingly, such patterns are all within the scope of the invention.

Unless otherwise indicated, all numbers expressing quantities of ingredients, volumes of fluids, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques. Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

The terms "a," "an," "the" and similar referents used in the context of describing the invention (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Certain embodiments of this invention are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the invention to be practiced otherwise than specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Furthermore, certain references have been made to patents and printed publications throughout this specification. Each of the above-cited references and printed publications are individually incorporated herein by reference in their entirety.

Specific embodiments disclosed herein may be further limited in the claims using consisting of or and consisting essentially of language. When used in the claims, whether as filed or added per amendment, the transition term "consisting of" excludes any element, step, or ingredient not specified in the claims. The transition term "consisting essentially of" limits the scope of a claim to the specified materials or steps and those that do not materially affect the basic and novel characteristic(s). Embodiments of the invention so claimed are inherently or expressly described and enabled herein.

In closing, it is to be understood that the embodiments of the invention disclosed herein are illustrative of the principles of the present invention. Other modifications that may be employed are within the scope of the invention. Thus, by way of example, but not of limitation, alternative configurations of the present invention may be utilized in accordance with the teachings herein. Accordingly, the present invention is not limited to that precisely as shown and described.

What is claimed is:

1. A compressed septum for insertion into an access port housing of a gastric band for the treatment of obesity, the compressed septum comprising:
    a septum including a first side and a second side;
    a top sheet in the form of a top ring having a first set of radially extending mating members, the top sheet positioned on the first side of the septum, and defining a cavity at a center portion of the top ring; and
    a bottom sheet in the form of a bottom ring having a second set of radially extending mating members, the bottom sheet positioned on the second side of the septum, and defining a cavity at a center portion of the bottom ring,
    wherein the second set of radially extending mating members of the bottom ring is configured to engage the first set of radially extending mating members of the top ring and cause the septum to be compressed such that the first side of the septum protrudes through the cavity of the top ring when the second set of radially extending mating members of the bottom ring and the first set of radially extending mating members of the top ring are bent to interlock with one another.

2. The compressed septum of claim 1 wherein the septum further includes a circumferential band positioned between the first side and the second side, and further wherein the second set of radially-extending mating members engages the first set of radially-extending mating members while contacting the circumferential band.

3. A compressed septum for insertion into an access port housing of a gastric band for the treatment of obesity, the compressed septum comprising:
    a septum including a first side and a second side;
    a top ring having a first set of radially extending mating members positioned on the first side of the septum, and defining a cavity at a center portion of the top ring; and
    a bottom ring having a second set of radially extending mating members positioned on the second side of the septum, and defining a cavity at a center portion of the bottom ring,
    wherein the second set of radially extending mating members of the bottom ring is configured to engage the first set of radially extending mating members of the top ring and cause the septum to be compressed such that the first side of the septum protrudes through the cavity of the top ring when the second set of radially extending mating members of the bottom ring and the first set of radially extending mating members of the top ring are bent to interlock with one another,
    wherein each of the first set of radially-extending mating members and each of the second set of radially-extending mating members are "L-shaped" fingers.

4. The compressed septum of claim 3 wherein each mating member of the first set of radially-extending mating members contacts and interlocks with a mating member of the second set of radially-extending mating members.

5. A compressed septum for insertion into an access port housing of a gastric band for the treatment of obesity, the compressed septum comprising:
    a septum including a first side and a second side;
    a top ring having a first set of radially extending mating members positioned on the first side of the septum, and defining a cavity at a center portion of the top ring; and
    a bottom ring having a second set of radially extending mating members positioned on the second side of the septum, and defining a cavity at a center portion of the bottom ring,
    wherein the second set of radially extending mating members of the bottom ring is configured to engage the first set of radially extending mating members of the top ring and cause the septum to be compressed such that the first side of the septum protrudes through the cavity of the top ring when the second set of radially extending mating members of the bottom ring and the first set of radially extending mating members of the top ring are bent to interlock with one another,
    wherein the second set of radially-extending mating members is configured to engage the first set of radially-extending mating members to exert lateral compression on the septum, and
    wherein the lateral compression on the septum is configured to cause the septum to protrude out of the cavities of the top ring and the bottom ring.

6. The compressed septum of claim 5 wherein the top ring and the bottom ring are constructed out of titanium.

7. A pre-loaded septum for insertion into an access port housing of a gastric band for the treatment of obesity, the pre-loaded septum comprising:
a septum including a first side and a second side;
a first washer-shaped titanium metal sheet positioned on the first side of the septum, the first washer-shaped titanium metal sheet defining a cavity at a center portion of the first washer-shaped titanium metal sheet, the first washer-shaped titanium metal sheet further including a first set of radially-extending mating members; and
a second washer-shaped titanium metal sheet positioned on the second side of the septum, the second washer-shaped titanium metal sheet defining a cavity at a center portion of the second washer-shaped titanium metal sheet, the second washer-shaped titanium metal sheet further including a second set of radially-extending mating members configured to interlock the first set of radially-extending mating members.

8. The pre-loaded septum of claim 7 wherein the second set of radially-extending mating members are further configured to interlock the first set of radially-extending mating members when both sets of radially-extending mating members are bent towards each other.

9. The pre-loaded septum of claim 8 wherein the septum further includes a circumferential band positioned between the first side and the second side, and further wherein the second set of radially-extending mating members interlocks the first set of radially-extending mating members while contacting the circumferential band.

10. The pre-loaded septum of claim 9 wherein each of the first set and the second set of radially-extending mating members is a "L" shaped finger.

11. The pre-loaded septum of claim 9 wherein each mating member of the first set contacts and interlocks with a different mating member of the second set.

12. The pre-loaded septum of claim 7 wherein the second set of radially-extending mating members is configured to engage the first set of radially-extending mating members to exert lateral compression on the septum.

13. The pre-loaded septum of claim 12 wherein the lateral compression on the septum is configured to cause the septum to protrude out of the cavities of the first washer-shaped titanium metal sheet and the second washer-shaped titanium metal sheet.

14. A gastric banding system for the treatment of obesity, the gastric banding system comprising:
a gastric band disposed about an upper-stomach region, the gastric band including an inflatable portion configured to be inflated with the addition of fluid and deflated with the removal of fluid;
an access port fluidly connected to the inflatable portion of the gastric band via a connecting tube, the access port penetrable by a syringe for receiving the fluid to be added to the inflatable portion and for delivery of fluid from the inflatable portion to the syringe, the access port including:
a housing defining a septum-receiving portion and a fluid reservoir for holding of the fluid received by the syringe or the fluid to be delivered to the syringe, and
a pre-loaded septum positioned within the septum-receiving portion, the pre-loaded septum having:
a rubber member including a first side and a second side,
a top compressing sheet positioned on the first side of the rubber member, the top compressing sheet including a first inner ring defining a cavity at a center portion of the top compressing sheet, the top compressing sheet further including a first set of radially-extending mating members, and
a bottom compressing sheet positioned on the second side of the rubber member, the bottom compressing sheet including a second inner ring defining a cavity at a center portion of the bottom compressing layer, the bottom compressing sheet further including a second set of radially-extending mating members configured to engage the first set of radially-extending mating members,
wherein at least one of the first set and second set of radially-extending mating members is bent to interlock with the other of the first set and second set of radially-extending mating members.

15. The gastric banding system of claim 14 further including a fluid seal positioned within the septum-receiving portion of the access port housing and interfacing between the pre-loaded septum and the access port housing.

16. The gastric banding system of claim 15 wherein the fluid seal is constructed out of a rubber material of a first durometer, and the rubber member of the pre-loaded septum is constructed out of a rubber material of a second durometer higher than the first durometer.

17. The gastric banding system of claim 15 wherein the rubber member further includes a circumferential band positioned between the first side and the second side, and further wherein the second set of radially-extending mating members engages the first set of radially-extending mating members while contacting the circumferential band.

18. The gastric banding system of claim 14 wherein the top compressing sheet and the bottom compressing sheet are constructed out of a titanium material.

19. A gastric banding system for the treatment of obesity, the gastric banding system comprising:
a gastric band disposed about an upper-stomach region, the gastric band including an inflatable portion configured to be inflated with the addition of fluid and deflated with the removal of fluid;
an access port fluidly connected to the inflatable portion of the gastric band via a connecting tube, the access port penetrable by a syringe for receiving the fluid to be added to the inflatable portion and for delivery of fluid from the inflatable portion to the syringe, the access port including:
a housing defining a septum-receiving portion and a fluid reservoir for holding of the fluid received by the syringe or the fluid to be delivered to the syringe, and
a pre-loaded septum positioned within the septum-receiving portion, the pre-loaded septum having:
a rubber member including a first side and a second side,
a top compressing layer positioned on the first side of the rubber member, the top compressing layer including a first inner ring defining a cavity at a center portion of the top compressing layer, the top compressing layer further including a first set of radially-extending mating members, and
a bottom compressing layer positioned on the second side of the rubber member, the bottom compressing layer including a second inner ring defining a cavity at a center portion of the bottom compressing layer, the bottom compressing layer further including a second set of radially-extending mating members configured to engage the first set of radially-extending mating members,
wherein at least one of the first set and second set of radially-extending mating members is bent to interlock with the other of the first set and second set of radially-extending mating members,
wherein each of the first set and the second set of radially-extending mating members is an "L" shaped finger.

20. The gastric banding system of claim 19 wherein each mating member of the first set contacts and interlocks with a different mating member of the second set.

21. The gastric banding system of claim 19 wherein the second set of radially-extending mating members is configured to engage the first set of radially-extending mating members to exert lateral compression on the rubber member.

22. The gastric banding system of claim 19 wherein a lateral compression on the rubber member is configured to cause the rubber member to protrude out of the cavities of the top compressing layer and the bottom compressing layer.

* * * * *